(12) United States Patent
Han et al.

(10) Patent No.: US 6,475,750 B1
(45) Date of Patent: Nov. 5, 2002

(54) GLUCOSE BIOSENSOR

(75) Inventors: In Suk Han, Salt Lake City, UT (US); You Han Bae, Salt Lake City, UT (US); Dal Young Jung, Salt Lake City, UT (US); Jules John Magda, Salt Lake City, UT (US)

(73) Assignee: M-Biotech, Inc., Salt Lake City, UT (US)

( * ) Notice: Subject to any disclaimer, the term of this patent is extended or adjusted under 35 U.S.C. 154(b) by 15 days.

(21) Appl. No.: 09/644,323

(22) Filed: Aug. 23, 2000

Related U.S. Application Data

(63) Continuation-in-part of application No. 09/308,392, filed on May 11, 1999, now Pat. No. 6,268,161.
(60) Provisional application No. 60/151,054, filed on Aug. 27, 1999.

(51) Int. Cl.[7] ................................................. C12Q 1/54
(52) U.S. Cl. ........................ 435/14; 435/26; 435/287.1; 436/95; 436/148; 604/891.1; 604/892.1
(58) Field of Search ........................... 435/14, 25, 26, 435/287.1; 436/95, 148; 604/891.1, 892.1

(56) References Cited

U.S. PATENT DOCUMENTS

| | | |
|---|---|---|
| 3,869,676 A | 3/1975 | Harrison et al. |
| 3,883,812 A | 5/1975 | Harrison et al. |
| 4,703,756 A | 11/1987 | Gough et al. |
| 4,919,141 A | 4/1990 | Zier et al. |
| 5,141,873 A | 8/1992 | Steudle et al. ............... 436/148 |
| 5,305,745 A | 4/1994 | Zacouto ........................ 128/637 |
| 5,372,133 A | 12/1994 | Hogen Esch |
| 5,431,160 A | 7/1995 | Wilkins |
| 5,544,651 A | 8/1996 | Wilk ............................. 128/633 |
| 5,593,852 A | 1/1997 | Heller et al. .................... 435/14 |
| 5,665,065 A | 9/1997 | Colman |
| 5,752,918 A | 5/1998 | Fowler et al. ................ 600/488 |
| 5,967,975 A | 10/1999 | Ridgeway ..................... 600/300 |
| 5,995,860 A | 11/1999 | Sun et al. ..................... 600/341 |
| 6,030,827 A | 2/2000 | Davis et al. .............. 435/287.1 |
| 6,102,856 A | 8/2000 | Groff ............................ 600/301 |
| 6,113,539 A | 9/2000 | Ridenour ...................... 600/300 |
| 6,150,942 A | 11/2000 | O'Brien .................... 340/573.1 |
| 6,198,394 B1 | 3/2001 | Jacobsen et al. .......... 340/573.1 |
| 6,268,161 B1 * | 7/2001 | Han et al. ...................... 435/14 |

OTHER PUBLICATIONS

Albin, G.W., "Theoretical and Experimental Studies of Glucose Sensitive Membranes," J. Controlled Release, 1987, p. 267–291, vol. 6.

(List continued on next page.)

*Primary Examiner*—David A. Redding

(57) ABSTRACT

A biosensor (10) has a hydrogel (30) in a rigid and referably biocompatible enclosure (20). The hydrogel (30) includes an immobilized glucose-binding molecule such as concanavalin A (Con A) and an immobilized hexose saccharide such as a-D-mannopyranoside. The immobilized hexose saccharide competitively binds with free glucose to the glucose-binding molecules, thus changing the number of crosslinks in the hydrogel (30), which changes hydrogel swelling tendency and the pressure of the hydrogel in its confined space in proportion to the concentration of free glucose. By measuring the change in hydrogel pressure with a pressure transducer (40), the biosensor (10) is able to accurately measure the concentration of the tree glucose molecule without the problem of oxygen limitations and interference encountered by prior art biosensors. A battery (64) powered telemeter (60) operably engaged to the pressure transducer (40) sends a radio data signal to a receiver (66) containing an alarm system operably attached to a computer (62). Furthermore, an alarm system utilizes such a sensor to automatically notify a person that the blood glucose level is outside a predetermined parameter, and/or to automatically inject an agent such as glucose or glycogen which will raise blood glucose levels.

32 Claims, 15 Drawing Sheets-

OTHER PUBLICATIONS

Allcock. H. R., "Synthesis and Characterization of pH–Sensitive Ploy(organophosphazene) Hydrogels," Biomaterials, 1996, p. 2295–2302, vol. 17.

Bouin, J.C., "Relative Efficiencies of a Soluble and Immobilized Two–Enzyme System of Glucose Oxidase and Catalase,:" Biochim. Biophys. Acta, 1976, p. 23–36, vol. 438.

Bouin, J.C., "Parameters in the Construction of an Immobilized Dual Enzyme Catalyst," Biotechnol, Bioeng., p. 179–187, vol. 18.

Bronsted, H., Polyelectrolyte Gels; Properties, Preparation and Application, Am. Chem. Soc., 1992, p. 285–305, Washington, D.C.

Christakis, O.M., "On the Mechanism of Immobilized Glucose Oxidase Deactivation by Hydrogel Peroxide," Biotechnol. Bioengin., 1982, p. 2419–2439, vol. 21.

Ghandehari, H., "Biodegradable and pH Sensitive Hydrogels: Synthesis by a Polymer–Polymer Reaction," J. Marcrol. Chem. Phys., 1996, p. 197–980. vol. 197.

Gough, D.A. and Lucisano, "Transient Response of the Two–Dimensional Glucose Sensor," J., Anal. Chem., 1998, p. 1272–1281, vol. 60.

Gough, D.A., "Two–Dimensional Enzyme Electrode Sensor for Glucose," Anal. Chem., 1985, p. 2351–2357, vol. 57.

Gough, D.A., "Progress Toward a Potentially Implantable, Enzyme–Based Glucose Sensor," Diabetes Care, 1982, p. 190–198, vol. 5.

Ishihara, L., "Glucose Induced Permeation Control of Insulin through a Complex Membrane Consisting of Immobilized Glucose Oxidase and Poly(amino)," Polym. J., 1984, p. 625–631, vol. 16.

Ishihara, K., "Control of Insulin Permeation through a Polymer Membrane With Responsive Function for Glucose," Makrol. Chem. Rapid Commun., 1983, p. 327–331, vol. 4.

Ito, Y., "An Insulin–Releasing System that is Responsive to Glucose," J. Controlled Release, 1989, p. 195–203. vol. 10.

Jung. D.Y., "Catalase Effects on Glucose–Sensitive Hydrogels," Macrol., 2000, p. 3332–3336, vol. 9.

Kim, S. W., "Hydrogels: Swelling, Drug Loading, and Release," Pharm. Res., 1992, p. 283–290, vol. 9.

Klumb. L.A., "Design of Insulin Delivery Based on Glucose Sensitive Membranes," J. Controlled Release, 1992, p. 59–79, vol. 18.

Kost, J., "Glucose–Sensitive Membranes Containing Glucose Oxidase: Activity, Swelling and Permeability Studies," Biomed. Mater. Res., 1985, p. 1117–1133, vol. 19.

Krysteva, M.A., "Multienzyme Membranes for Biosensors," J. Chem. Tech, Biotech., 1992, p. 13–18, vol. 54.

Owusu, R.K., "Flow Microcalorimetric Study of Immobilized Enzyme Kinetics Using the Co–Immobilized Glucose Oxidase–Catalase System," Biochim. Biophys. Acta, 1986, p. 83–91, vol. 872.

Philippova, O., "pH–Responsive Gels of Hydrophobically Modified Poly(acrylic acid)," Macrol., 1997, p. 8278–8285, vol. 30.

Prenosil, J.E., "Immobilized Glucose Oxidase–Catalase and Their Deactivation in a Differential–Bed Loop Reactor," Biotechnol. Bioeng., 1979, p. 89–109, vol. 21.

Rao, J.K., "Implantable Controlled Delivery Systems for Proteins Based on Collagen–pHEMA Hydrogels," Biomaterials, 1994, p. 383–389, vol. 16.

Reach, G., "Can Continuous Glucose Monitoring Be Used for the Treatment of Diabetes," Anal. Chem., 1992, p. 381–386, vol. 64.

Sato, S., "Self–Regulating Insulin Delivery Systems," J. Controlled Release, 1984, p. 67–77, vol. 1.

Schott, H., "Kinetics of Swelling of Polymers and Their Gels," J. Pharm. Sci., 1992, p. 467–470, vol. 81.

Serres, A., "Temperature and pH–Sensitive Polymers for Human Calcitonin Delivery," Pharm. Res., 1996, p. 196–201, vol. 13.

Siegel, R.A., "pH–Dependent Equilibrium Swelling Properties of Hydrophobic Polyelectrolyte Copolymer Gels," Macromolecules, 1988, p. 3254–3259, vol. 21.

Teijon, J.M., "Cytarabine Trapping in Poly(2 hydroxyethyl methacrylate) Hydrogels: Drug Delivery Studies," Biomaterials, 1997, p. 383–388, vol. 18.

Vakkalanka, S.K., "Temperature– and pH–sensitive Terpolymers for Modulated Delivery of Streptokinase," J. Biomater, Poly. Sci., 1996, p. 119–129, ed. 8.

Wasserman, B.P., "High–Yield Method for Immobilization of Enzymes," Biotechnol Bioeng., 1980, p. 271–287, vol. 22.

Wilkins, E.S., "Towards Implantable Glucose Sensors: A Review," J. Biomed. Eng., 1989, p. 354–361, vol. 11.

Wingard, Jr., L. B., "Immobilized Enzyme Electrodes for the Potentiometric Measurement of Glucose Concentration: Immobilization Techniques and Materials," J. Biomed. Mater. Res., 1979, p. 921–935, vol. 13.

Shear Flows of Liquid Crystal Polymers: Measurements of the Second Normal Stress Difference and the Doi Molecular Theory. Magda et al. pp. 4460–4468. Reprinted from Macromolecules, vol. 24, No. 15, 1991.

A Diode–Quad Bridge Circuit for Use with Capacitance Transducers. Harrison et al. pp. 1468–1472, Rev. Sci, Instrum., vol. 44, No. 10, Oct. 1973.

Novel Rheological Techniques Applied to Investigative Rheology of Liquid Crystal Polymers. Seong Gi Baek. pp. v–68. A PhD Dissertation Defense. Sep. 1991.

Characterization of Glucose Dependent Gel–Sol Phase Transition of the Polymeric Glucose–Concanavalin A Hydrogel System. Obaidat et al. pp. 989–995. Pharmaceutical Research, vol. 13, No. 7, 1996.

Enzymatic Glucose Sensors: Improved Long–Term Performance In Vitro and In Vivo. Uplike et al. pp. 157–163. ASAIO Journal 1994.

Second normal stress difference of a Boger fluid. Magda et al. pp. 2000–2009. Polymer, 1991, vol. 32, No. 11.

Does $N_1$ or $N_2$ control the onset of edge fracture? Lee et al. pp. 306–308. Rheologica Acta, vol. 31, No. 2 (1992).

Measurement of the Second Normal Stress Difference for Star Polymers with Highly Entangled Branches. Lee et al. pp. 4744–4750. Macromolecules 1992, 25, 4744–4750.

Unusual pressure profiles and fluctuations during shear flows of liquid crystal polymers. Magda et al.

Concentrated entagled and semidilute entangled polystyrene solutions and the second normal stress difference. Magda et al.

Pressure Sensors Selection and Application. Duane Tandeske. pp. 77–115. Marcel Dekker, Inc. 1991.

A Pressure Telemetry System Utilizing a Capacitance–Type Transducer. Thomas B. Fryer. pp. 279–282. Biotelemetry III.

\* cited by examiner

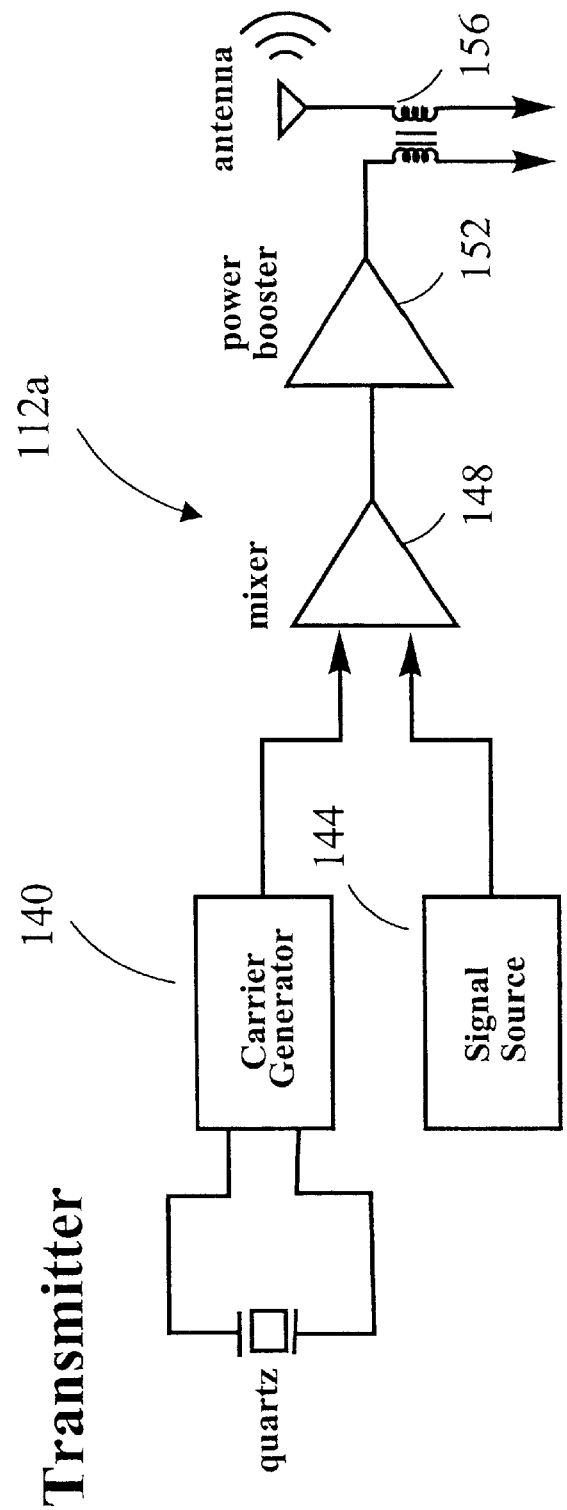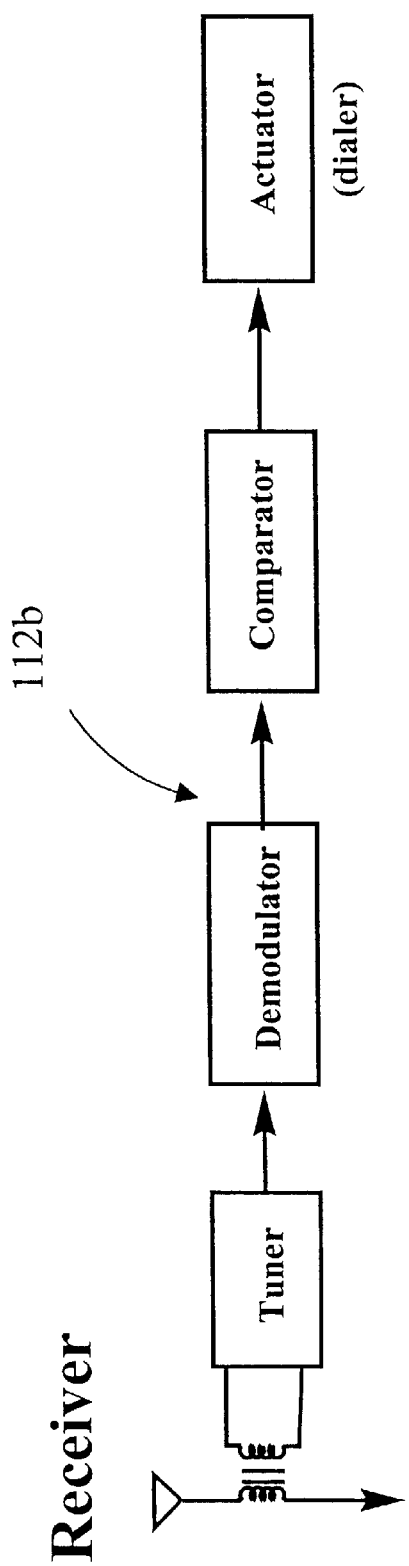
Fig. 13  Transmitter
Receiver

GLUCOSE BIOSENSOR

RELATED APPLICATIONS

The present application is a continuation-in part of U.S. patent application Ser. No. 09/308,392 and now U.S. Pat. No. 6,268,161, and claims the benefit of Provisional Patent Application Serial No. 60/151,054 Filed on Aug. 27, 1999.

STATEMENT OF GOVERNMENT INTEREST

This invention was made with government support under R43DK55958 (grant/contract no.) awarded by National Institute of Health. The Government has certain rights in the invention.

BACKGROUND OF THE INVENTION

1. Field of the Invention

This invention generally relates to a biosensor for measuring the concentration of glucose molecules in a solution, and more particularly to an implantable glucose monitoring device using a pressure transducer and a glucose sensitive hydrogel having an immobilized glucose binding molecules (GBM), an immobilized charged pendant group, and an immobilized hexose saccharide, the device being proportionally responsive to increases in glucose levels in the physiological fluids such as blood when it is implanted.

2. State of the Art

Diabetes is one of the major diseases in the United States. In 1995, there were approximately sixteen million Americans suffering from diabetes, including those undiagnosed. It is estimated that 650,000 new cases are diagnosed each year. Diabetes was the seventh leading cause of the death listed on U.S. death certificates in 1993, according to the National Center for Health Statistics. There are two major types of diabetes: type I diabetes (10% of diabetes cases in the United States), and type II diabetes (90% of diabetes cases in the United States). Type I diabetes is caused by an insulin deficiency due to the destruction of the pancreatic beta cells, and requires daily treatment with insulin to sustain life. Type II diabetes is caused by target organ insulin resistance resulting in a decreased responsiveness to both endogenous and exogenous insulin, and is usually managed by diet and exercise but may require treatment with insulin or other medication. Most people diagnosed with type II diabetes are over 40 years old.

Diabetes disturbs the body's ability to control tightly the level of blood glucose, which is the most important and primary fuel of the body. Insulin is a critical hormone needed to keep glucose concentrations within very narrow physiological limits in normal people though high levels of carbohydrates may be consumed. Not only is insulin secreted by the beta cells of the pancreas, but also its levels are rapidly regulated by glucose concentrations in the blood. Insulin allows the passage of glucose into the targets cells, which contain receptors for uptake of glucose. Diabetic patients with an elevated glucose level in the blood, hyperglycemia, have either an insulin deficiency or a decreased responsiveness to insulin. Hyperglycemia adversely affects other physiological processes. For example, hyperglycemia causes severe water loss and dehydration. Water loss can be so severe that it decreases blood pressure, and the reduced blood pressure may lead to brain damage. As discussed in National Diabetes Data Group, National Institutes of Health, National Institute of Diabetes and Digestive and Kidney Diseases, "Diabetes In America," 2nd edition, NIH Publication No. pp. 95–1468, (1995), patients of diabetes are often subject to destructive alterations of other physiological processes, causing blindness, heart attack, stroke, periodontal disease, neuropathy, nephropathy, and atherosclerosis resulting from hyperglycemia. Tissue damage can be so extensive that amputations are required to save the patient. Also, there is always the danger in diabetics of hypoglycemia due to diet, with an insulin injection required to bring the blood glucose level back up to normal. Hypoglycemic episodes can occur without the diabetic patient being aware of it. It is required to maintain a balance between insulin injection and glucose consumption to prevent hypoglycemia. However, the condition is not fatal if proper care is taken.

In treating diabetic patients, the aim is to tightly regulate the plasma glucose level within the normal physiological range (80–120 mg/dL), so that diabetic adverse effects can be avoided. Self-monitoring of blood glucose levels using dry chemical strips with a single drop of blood is considered a major advance in diabetes management. This in vitro method of monitoring of blood glucose. has two main disadvantages. The first is that sampling of blood is associated with the risk of infection, nerve and tissue damage, and discomfort to patients. The second disadvantage is the practical limitation in self-monitoring which arises because the sampling frequency is not great enough for tight control of blood glucose levels close to normal ranges over a 24-hr period. Thus, as an aid to diabetes therapy, continuous monitoring of blood glucose concentrations in vivo has long been recognized as a major objective as a future tool in the fight against diabetes.

During the past decade, intense effort has been directed toward the development of glucose monitoring biosensors as an aid to diabetes therapy. Development of an implantable glucose sensor that is specific to glucose and sensitive enough to precisely measure glucose levels in vivo would be a significant advance in the treatment of diabetes. Such ability to more closely control blood glucose levels would help prevent complications commonly brought on by diabetes. Such a sensor would also greatly facilitate glucose level data collection, glycemia research, and development of an insulin delivery system responsive to glucose levels in diabetic patients.

Several new implantable techniques have been developed for glucose analysis in clinical practice based on electrochemical principles and employing enzymes such as glucose oxidase (GOD) for glucose recognition. Potentially implantable glucose biosensors based on electrochemical transducers are the most highly developed, and this class of sensors can be further subdivided into potentiometric sensors, conductometric sensors, and amperometric sensors. The local pH change due to production of gluconic acid in the GOD reaction can be measured with a pH-selective electrode or an ion selective field effect transistor (ISFET), which is the basis of the potentiometric method. Similarly, in the conductometric method, changes in the electrical resistance due to the progress of the GOD reaction are measured. At present, neither the potentiometric method nor the conductometric method appears to be suitable for in vivo glucose monitoring due to: (a) interference by species other than glucose in the physiological environment; (b) low sensitivity and logarithmic dependence of the signal on the glucose concentration. A linear dependence of the signal on glucose concentration is highly desirable because of the need for repeated recalibrations over time for implanted glucose sensors. However, non-linear calibration curves can be handled reasonably well using microprocessors.

The most advanced glucose sensors for in vivo monitoring are electrochemical sensors using the amperometric technique, possibly because they do offer the possibility for a linear calibration curve. In the amperometric method, an electrode is used which produces a current proportional to the diffusional flux of hydrogen peroxide ($H_2O_2$) to the electrode surface, or, alternatively, proportional to the diffusional flux of oxygen ($O_2$) to the electrode surface. A membrane layer containing immobilized GOD surrounds the electrode. The glucose reaction catalyzed by GOD produces hydrogen peroxide and consumes oxygen. An increase in the surrounding glucose concentration should increase the diffusional flux of glucose into the membrane and increase the reaction rate within the membrane. The increase in reaction rate in turn should increase the local hydrogen peroxide concentration and decrease the local oxygen concentration within the membrane. This should lead to an increase in the current detected by a hydrogen peroxide-based electrode sensor, or a decrease in current as detected by an oxygen-based electrode sensor. The latter approach, based on detecting the oxygen flux, also requires a second oxygen-based electrode sensor located in a hydrogel without the GOD enzyme. This second electrode is used as a reference.

Amperometric sensors must overcome several hurdles before they will ever be useful for commercial in vivo monitoring. Current glucose sensor designs appear unlikely to solve these difficult problems in the near future. The first hurdle arises from electrochemical interference. The analyte (whether hydrogen peroxide or oxygen) must be the only species present which produces a current at the electrode. Hence for both oxygen-based and hydrogen peroxide-based glucose sensors, an inner membrane must be used which is permeable to the analyte but impermeable to endogenous interferents. This is a difficult goal to achieve due to the heavily "contaminated" nature of blood. Secondly, for the hydrogen peroxide-based sensor, mass transfer coefficients for diffusion of glucose and oxygen into the membrane containing GOD must not change with time due to an adsorbed layer. Thirdly, for both types of amperometric sensors, GOD must not deactivate with time. In clinical studies of the hydrogen peroxide-based sensor, decay in sensitivity over the implant period was observed, a phenomenon that could not be explained by blockage of the sensor surface by protein. One possible explanation for the loss of sensitivity is hydrogen peroxide mediated GOD deactivation. For the oxygen-based sensor, this can be avoided by co-immobilizing catalase with GOD, because catalase consumes hydrogen peroxide. Fourthly, a shortage of oxygen relative to glucose can place an upper limit on the biosensor's ability to measure glucose levels. This problem is called the "oxygen deficit".

In addition to the biosensors described above, several glucose release mechanisms have been developed to release insulin directly into a diabetic's bloodstream in response to high glucose levels. One approach is to use in a hydrogel a chemically immobilized pendant group which is charged at the physiological solution conditions (pH2 to pH10), a chemically immobilized hexose saccharide such as glucose, galactose, and mannose in the hydrogel, and an immobilized glucose binding molecule (CBM) such as for example, glucokinase, GOD, xylose isomerase, boronic acids, or lectins including isolectin I and Concanabvalin A (Con A) in the hydrogel. The hydrogel swells with increases in glucose concentration using essentially the same physical phenomenon that will be employed in the glucose biosensor, described below. The amount of swelling in the insulin delivery devices was used to control insulin permeability through a hydrogel membrane. Using essentially the same hydrogel-swelling phenomenon, as discussed shortly, the proposed biosensor infers changes in glucose concentration from changes in hydrogel crosslinking density, swelling tendency, and pressure exerted in the enclosure. The decrease in hydrogel crosslinking density and the increase of the swelling tendency of the hydrogel is proportional to glucose concentration as a result of competitive binding between immobilized hexose saccharide and free glucose to the immobilized GBM in the polymer backbone which has high affinity to glucose. The prior art does not teach the use of the glucose-induced swelling of the hydrogel as a method of measuring glucose concentrations. The prior art specifically does not teach the use of a pressure transducer to measure hydrogel swelling in response to increases in glucose levels in the blood, the use of the pressure transducer providing a measurement tool that avoids the problems encountered by electrochemical methods of the prior art, described above. The present invention avoids the problems of prior art biosensors such as interference, enzyme degradation, and oxygen deficit and provides further related advantages as described in the following summary.

SUMMARY OF THE INVENTION

The present invention teaches certain benefits in construction and use that will give rise to the objectives described below.

The present invention provides a biosensor for measuring the concentration of glucose in a solution. The biosensor includes a hydrogel in a rigid and preferably biocompatible enclosure. The hydrogel includes an immobilized hexose saccharide, such as α-D-mannopyranoside, and an immobilized GBM, such as concanavalin A (Con A), having high affinity to free glucose and the immobilized hexose saccharide (or a pendant glucose). The GBM and hexose saccharide are chemically immobilized or physically immobilized on the backbone of the hydrogel. The hydrogel is in a de-swelled form when there is no free glucose due to the tight binding between Con A and the immobilized glucose or hexose saccharide. However, the hydrogel swells in a proportion to the concentration of free glucose due to competitive binding of the free glucose with the immobilized hexose saccharide to immobilized GBM such as Con A. When the free glucose binds to the GBM, this reduces hydrogel crosslinking density, thereby increasing hydrogel swelling tendency and increasing the pressure exerted by the swelling hydrogel in the enclosure.

By measuring the change in pressure with a means for measuring, preferably a pressure transducer, the biosensor is able to accurately measure the concentration of the free glucose without the problem of interference encountered by prior art biosensors. Since the binding of free glucose to the GBM does not require oxygen, the proposed biosensor measures free glucose without the problem of oxygen deficit encountered by prior art biosensor. Additionally, since the proposed biosensor does not produce hydrogen peroxide, the problem of hydrogen peroxide-induced enzyme degradation encountered by prior art biosensors can be avoided. A means for reporting the concentration of the glucose, preferably a battery powered telemeter, is operably engaged with the means for measuring, and sends a radio data signal to a receiver operably attached to a computer with an alarm system.

A primary objective of the present invention is to provide a biosensor having advantages not taught by the prior art.

Another objective is to provide a biosensor that is extremely sensitive to the concentration of glucose, and also relatively free from interference, even when operating in complex media such as human blood.

A further objective is to provide a biosensor that directly measures changes in free glucose, rather than the indirect parameters measured by electrodes. This is especially critical in implantable biosensors because this frees the present invention from potential sources of interference as well as alleviates the need for oxygen that is essentially required for the GOD reaction.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The above and other objects, features and advantages of the invention will become apparent from a consideration of the following detailed description presented in connection with the accompanying drawings in which:

FIG. 13 is a schematic diagram of the transmitter and receiver;

DETAILED DESCRIPTION

Figure 1:
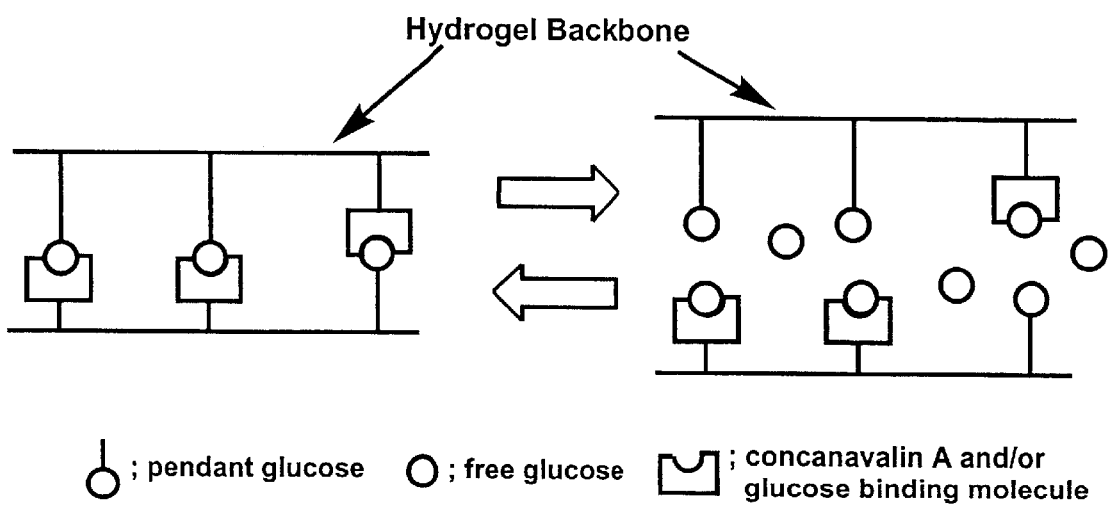
FIG. 1 is an example of the competitive binding and swelling mechanism.
Figure 2:
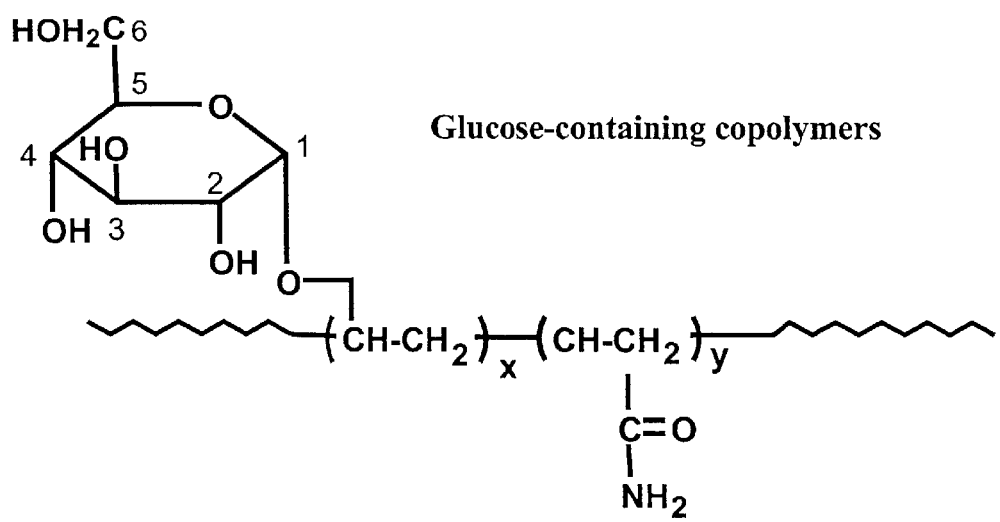
FIG. 2 is an example of a glucose-containing copolymer.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

The above-described drawing figures illustrate the invention, a biosensor 10 for measuring the concentration of glucose in a solution. In its broadest description, the biosensor 10 uses a special polymeric hydrogel 30 that swells in proportion to the concentration of free glucose. Con A or other GBM is immobilized in the hydrogel 30, and free glucose competitively binds with an immobilized hexose saccharide such as glucose to Con A, reducing hydrogel crosslinks and thereby causing the hydrogel 30 to swell and increasing the pressure of the hydrogel in its enclosure. The biosensor 10 has a means for measuring 40 the pressure of the hydrogel 30, and a means for reporting 60 the concentration of glucose based on the measured pressure of the hydrogel 30. In its preferred embodiment, the biosensor 10 includes a rigid, biocompatible enclosure 20 having semi-permeable membrane 26 covering an open end 22, a flexible diaphragm 28 between the semipermeable membrane 26 and the closed end 24, and a polymeric hydrogel 30 enclosed therebetween, the hydrogel 30 including moieties that cause the hydrogel 30 to swell in proportion to the free glucose diffusing into the hydrogel 30.

The enclosure 20 is designed to be implanted directly into the human body for monitoring blood glucose levels of diabetics. In this embodiment, the biosensor 10 uses Con A immobilized in a hydrogel 30. The means for measuring 40 the pressure of the hydrogel 30 is preferably a pressure transducer 40 operably associated with the flexible diaphragm 28. The means for reporting 60 glucose levels is preferably a battery 64 operated telemeter 60 that sends a radio data signal to a receiver operably attached to a computer 62. Alternative embodiments of this biosensor 10 can easily be adapted by those skilled in the art. The biosensor 10 can measure free glucose by replacing Con A with an appropriate GBM having specifically high affinity to glucose such as GOD, glucokinase, xylose isomerase, boronic acids, and isolectin I. Rather than use of a telemeter 60, a direct electrical connection to a computer 62 can be used when the biosensor 10 is a minimally invasive implant into a human body. While the pressure transducer 40 is currently the preferred tool for measuring changes in the pressure of the hydrogel 30, those skilled in the art can devise alternative means of measuring and reporting changes in the pressure of the hydrogel 30. One alternative method is to use a piezoresistive sensor in place of the pressure transducer 40.

The Enclosure, Semipermeable Membrane, and Diaphragm

Figure 3:
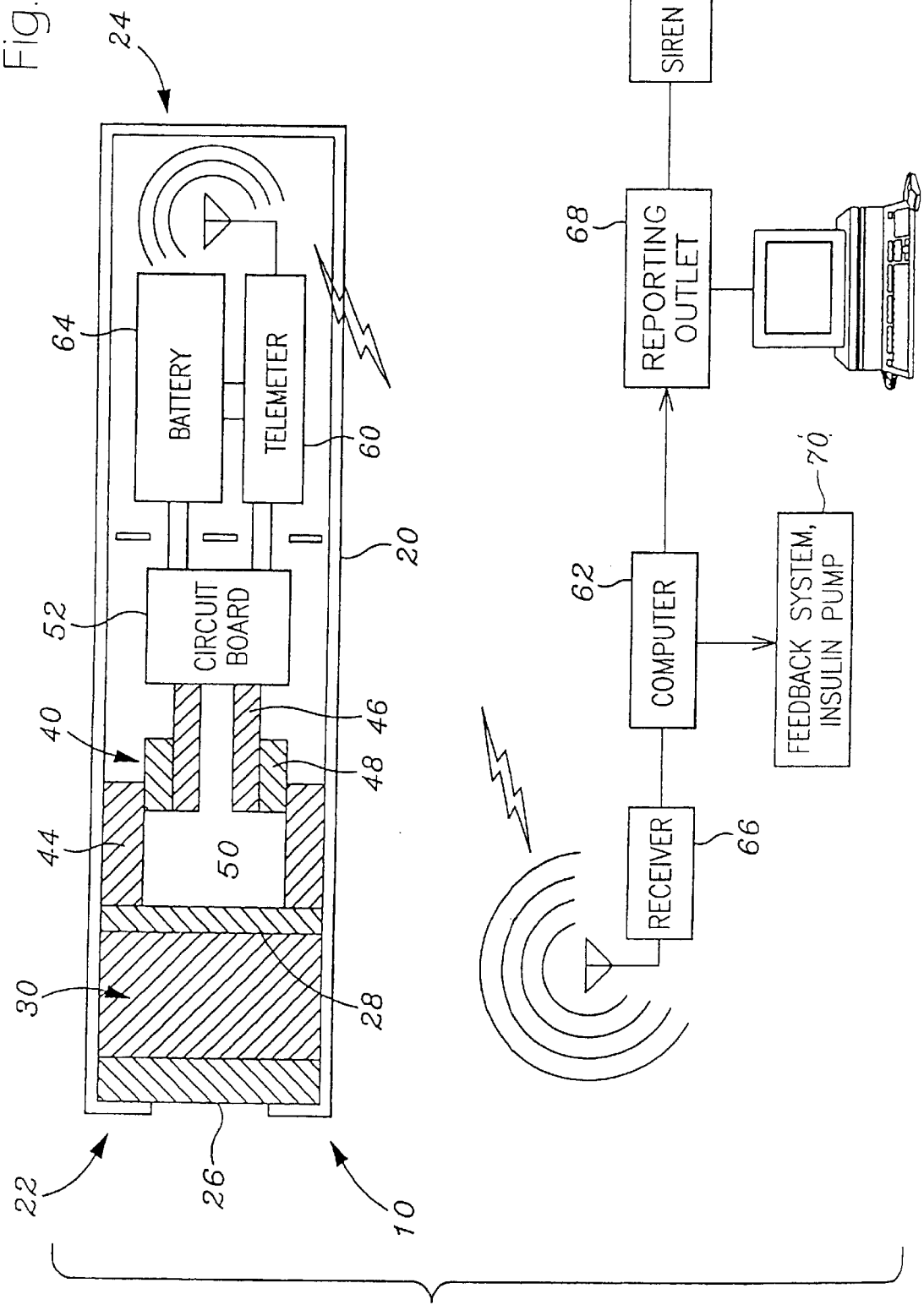
FIG. 3 is a side, partial cross-sectional view and diagram of the preferred embodiment of the present invention, showing a biosensor that can be implanted under a diabetic's skin.

As best shown in FIG. 3, the structure of the biosensor 10 is provided by an enclosure 20, preferably a cylindrical enclosure 20 having an open end and a closed end. The open end is sealed with a semipermeable membrane 26. A flexible diaphragm 28 is mounted between the semipermeable membrane 26 and the closed end. The hydrogel 30, described below, is enclosed between the semipermeable membrane 26 and the diaphragm 28. The enclosure 20 is preferably constructed of a rigid, impermeable, and biocompatible material such as stainless steel; and the enclosure 20 is preferably conjugated with heparin to prevent blood clotting, and polyethylene glycol (PEG) to decrease the body's immune response against the enclosure 20. The enclosure 20 is preferably coated with a biocompatable material such as a thin polymer. The enclosure 20 is preferably cylindrical in shape to facilitate implantation, the cylinder being approximately 5 to 12 mm long and having a diameter of approximately 0.1 to 3 mm. If the enclosure 20 will not be implanted, any rigid and impermeable material such as fiber, plastic or metal can be used.

The semipermeable membrane 26 is permeable to the passage of glucose, and gluconic acid; however, it is impermeable to the passage of blood clots, cells, proteins, lectins, and the hydrogel 30. The semipermeable membrane 26 is preferably made of a material rigid enough to sustain the pressure of a swollen glucose sensitive hydrogel 30. If the biosensor 10 is to be implanted into the human body, the semipermeable membrane 26 is preferably an inert, nontoxic material. A suitable semipermeable material can be selected from, but is not limited to, the following groups of polymers: cellulose acetate, methyl cellulose, polyvinyl alcohol, and polyurethane. The semipermeable materials are also preferably conjugated with heparin and polyethlyene glycol (PEG) to decrease immunogenic response, blood clotting and cell attachment on the surface. Examples of such enclosures and semipermeable membranes are discussed in Heller, U.S. Pat. No. 5,593,852, Wilkins, U.S. Pat. No. 5,431,160, Hogen Esch, U.S. Pat. No. 5,372,133, Zier, U.S. Pat. No. 4,919,141, and Gough, U.S. Pat. No. 4,703,756, all hereby incorporated in full by reference. Additionally, a biodegradable material that will fall off, layer-by-layer, carrying the fibrogeneous material with it can be coated to on the semipermeable membrane.

The diaphragm 28 is preferably a flexible but conductive material useful for use with a transducer 40. Such diaphragms are known in the art. The preferred diaphragm 28 is made of an alloy sold under the trademarks KOVAR™ or INVAR 36™ by Hamilton Technology, Inc., of Lancaster, Pa. The diaphragm 28 thickness is preferably approximately 12.5 $\mu$m to achieve optimum spot welding and sensitivity. Such a diaphragm is described in Baek S G. Ph.D. Thesis, University of Utah, (1992). The diaphragm 28 is preferably seal welded to the enclosure 20 between the semipermeable membrane 26 and the closed end 24 of the enclosure 20. The hydrogel 30 fills the chamber within the enclosure 20 between the semipermeable membrane 26 and the diaphragm 28. The means for measuring 40 and the means for reporting 60, described below, are located in the chamber within the enclosure 20 between the diaphragm 28 and the closed end 24 of the enclosure 20.

Concanavalin A

Summer and Howell first isolated Con A from jack bean. Con A has been shown to have significant biological properties such as binding of specific saccharides with high affinity. Con A, containing 238 amino acid residues and having a molecular weight of 27,000, exists as dimers in solution at pH below 6 and as tetramers at physiologic pH. The metal ions, usually Mn+2 or Ca+2, play an essential role in stabilizing the formation of the specific saccharide binding site. The binding properties of Con A to specific saccharides are changed by various conditions such as ionic strength, temperature, and pH. Con A shows maximum binding activity to saccharide at pH between 6 to 7. Con A alters its binding activity at high pH, above pH 9, due to its conformational changes. Tetrameric forms are favored to bind with specific saccharides. At higher temperature, Con A forms tetramers. As an example, increasing the temperature 4° C. to 37° C. significantly enhances precipitation of dextran by Con A. However, Con A is denatured above 50° C. like most proteins. Con A exists as dimers at lower ionic strength.

Immobilization of Concanavalin A and Glucose to the Polymer Backbone of the Hydrogel A minimal configurational structure of saccharides such as unmodified hydroxyl groups on the C-3, C-4, and C-6 position in a hexose is essential for binding to Con A with high affinity. The binding affinity of a hexose saccharide is dependent upon the configurational factor at C2 hydroxyl group, since mannose with the axial position at C2 hydroxyl group has 40 times higher binding affinity than mannose with the equatorial position at C2 hydroxyl group.

A vinyl group is preferably attached to C1 of glucose (allyl glucose; AG) and Con A through etherification reaction of glucose with allyl alcohol and nucleophilic reaction of Con A with metaacryloyl chloride. C3, C4, and C6 hydroxyl groups of AG are preferably not modified as described (Obaidat, A A., and Park, K. Pharmaceutical Research 13: 989–995, 1996). Copolymerization of AG and modified Con A with cross-linking agents and monomers such as acrylamide and hydroxylethyl methacrylate (HEMA) preferably occurs by a free radical reaction. The polymer chain preferably contains glucose and Con A as pendant groups. The hydrogel thus formed is preferably porous. The porosity is preferably controlled with several methods such as bubbling or excessive addition of powdered salt to the copolymerization reaction. The hydrogel preferably swells when free glucose is introduced into the hydrogel due to competitive binding between free glucose with immobilized glucose to immobilized Con A in the hydrogel. The swelling ratio is preferably proportional to free glucose concentrations in the solution. The reaction ratios of AG and modified Con A, monomer, and cross-linking agents are preferably optimized to give a measurable pressure with a pressure transducer resulting from swelling and de-swelling of the hydrogel due to changing free glucose concentrations. Alternatively, p-nitrophenyl-$\alpha$-D-mannopyranoside, and p-nitrophenyl-$\alpha$-D-glucopyranoside can be used for immobilization on the polymer instead of glucose. Also, other GBMs such as GOD, glucokinase, xylose isomerase, boronic acids, and isolactin I can be physically or chemically immobilized on the polymer instead of Con A.

Means for Measuring—Pressure Transducer

The biosensor includes a means for measuring 40 the pressure of the hydrogel. This element is critical. While prior art biosensors rely on direct measurement of the GOD catalyzed chemical reaction with an electrode, measurement of the increase in hydrogel pressure and free glucose induced swelling has never been used in the prior art. A biosensor 10 that directly relies on changes in free glucose concentration avoids an important source of outside interference. Free glucose itself is directly measured rather than the indirect parameters measured by electrodes.

Figure 6:
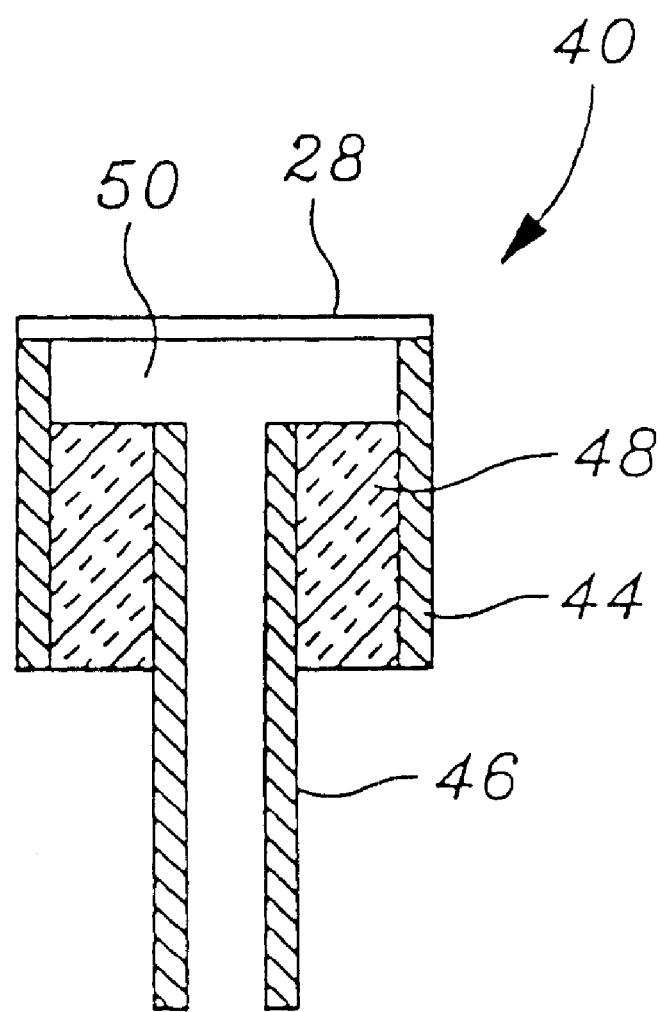
FIG. 6 is side elevational sectional view of the pressure transducer.
Figure 7:
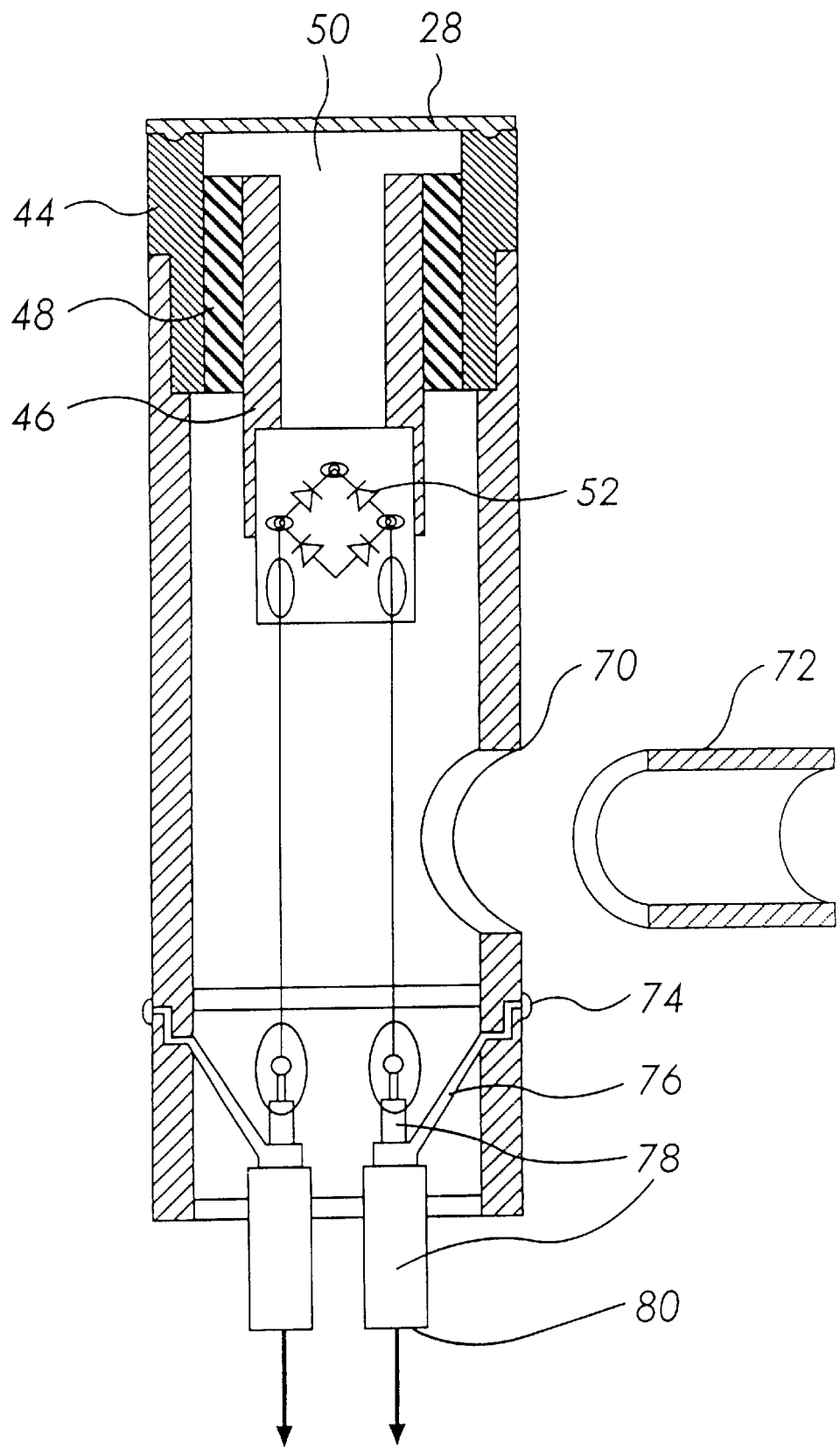
FIG. 7 is side elevational sectional view of the pressure transducer including the preferred circuit board having miniature diodes, which are part of a diode quad bridge circuit.
Figure 8:
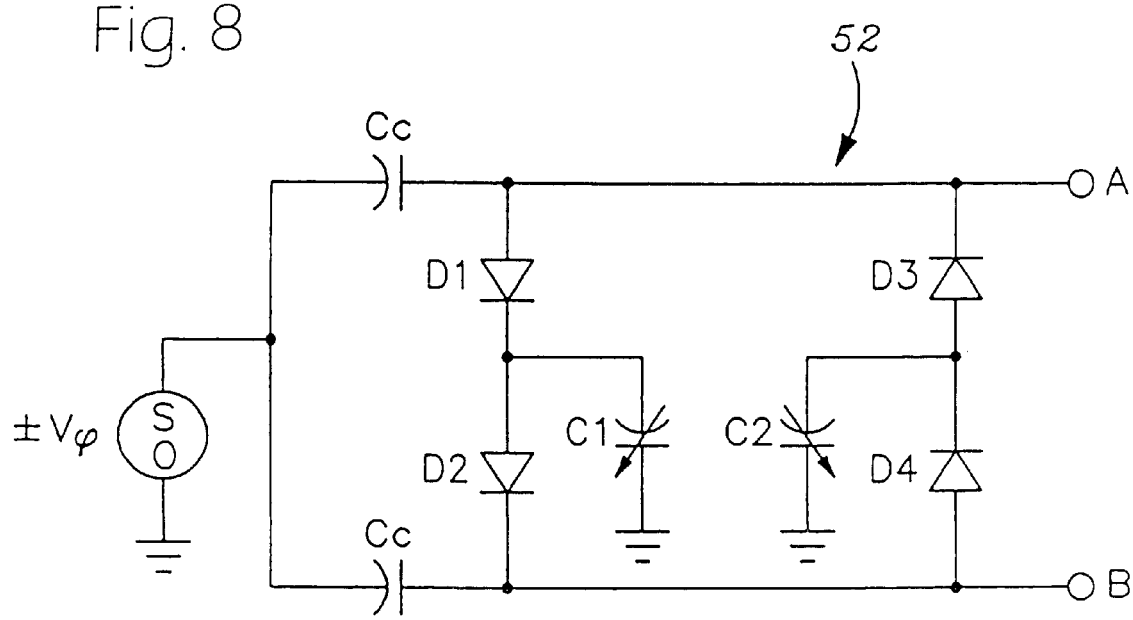
FIG. 8 is an electrical schematic showing the preferred diode quad bridge circuit.

As shown in FIGS. 6–7, the means for measurement is preferably a pressure transducer 40. Pressure transducers are known in the art and those skilled in the field can construct a transducer optimized to the specific needs of the biosensor 10. An example of a transducer is disclosed in Harrison D R, Dimeff J. Rev. Sci. Instrum. 44:1468–1472, (1973) and Harrison et al., U.S. Pat. No. 3,869,676, titled Diode-Quad Bridge Circuit Means, hereby incorporated by reference.

As shown in FIG. 7, the biosensor 10 can also include a calibration hole 70 which receives a small brass tube 72, a solder stranded copper wire 74, a braided shield 76, insulators 78 and coaxial cables 80.

In its most preferred embodiment, the means for measuring 40 is a capacitive pressure transducer 40 associated with the flexible diaphragm 28 described above. The preferred transducer 40 includes a first electrode 44 and a second electrode 46, the first and second electrodes 44 and 46 being separated by an insulator 48. In its preferred embodiment, the first and second electrodes 44 and 46, as well as the insulator 48, are coaxially aligned cylinders. The flexible diaphragm 28 is preferably welded to the top of the first conductor 44, converting the diaphragm 28 into one of the electrodes of a capacitor portion of the transducer 40. The first electrode 44 is connected to the diaphragm 28, and the diaphragm 28 is separated from the second electrode 46 by an air gap 50.

Since the diaphragm 28 is in mechanical contact with the hydrogel 30, the diaphragm 28 deflects in response to changes in the pressure of the hydrogel 30, thereby changing the size of the air gap 50 between the second electrode 46 and the diaphragm 28, thereby changing the value of the capacitance. The value of the capacitance change is detected remotely, preferably using a diode quad bridge circuit 52. These pressure transducers 40 have been successfully used to measure pressure changes in flowing polymeric liquids as small as one Pascal.

Examples of alternative transducers are described in Takaki, U.S. Pat. No. 5,711,291 and Fowler, U.S. Pat. No. 5,752,918, hereby incorporated by reference. A more detailed discussion of transducers can be found in the following references, hereby incorporated by reference: Baek S G. Ph.D. Thesis, University of Utah, (1991); Magda J J, Baek S G, Larson R G, DeVries K L. Polymer 32:1794–1797, (1991); Magda J J, Baek S G, Larson R G, DeVries K L. Macromolecules 24:4460–4468, (1991); Magda J J, Lou J, Baek S G. Polymer 32:2000–2009, (1991); Lee C S, Tripp B, Magda J J. Rheologica Acta 31:306–308, (1992); Lee C S, Magda J J, DeVries K L, Mays J W. Macromolecules 25:4744–4750, (1992); Magda J J, Baek S G. Polymer 35:1187–1194, (1994); Fryer T. *Biotelemetry III*, Academic Press, New York, pp.279–282, (1976); Tandeske, D., Chapter 5 in Pressure Sensors Selection and Application, Marcel Dekker, New York, 1991; Updike S J, Shults M C, Rhodes R K, Gilligan B J, Luebow J O, von Heimburg D. ASAIO J. 40:157–163, (1994); and Foulds N C, Frew J E, Green M J. Biosensors A Practical Approach (Cass AEG. eds.) IRL Press Oxford University, pp. 116–121, (1990).

While a preferred pressure transducer 40 has been described, those skilled in the art can devise other means for measuring 40. Other alternative embodiments include a piezoelectric transducer or sensor and a piezoresistive pressure sensor. Other means for measuring pressure or increase in volume could also be used. These alternatives are considered equivalent to the described invention.

Means for Reporting—Telemeter

Figure 4:
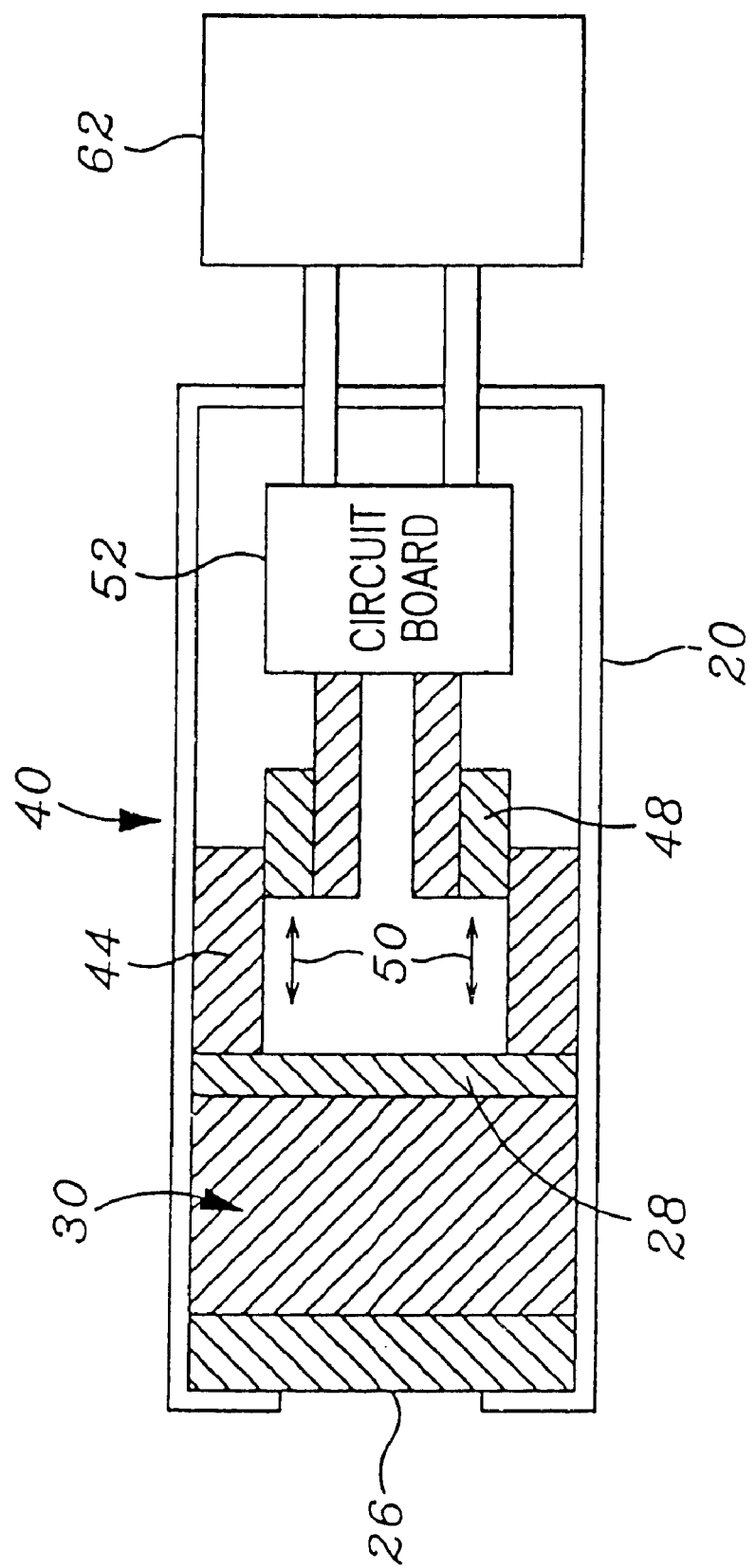
FIG. 4 is a side partial cross-sectional view of an alternative embodiment thereof, showing a biosensor that is electronically attached to a computer.

Finally, the biosensor 10 includes a means for reporting 60 the concentration of the organic molecule once it has been measured. This element will vary greatly depending upon the specific use of the biosensor 10 as well as the needs of the user. In its simplest form, as shown in FIG. 4, the transducer 40 is simply connected electronically to a computer means, generally a personal computer. The computer compares the data from the transducer 40 to a calibration curve to generate usable data for export through a reporting means. In one embodiment, the computer sounds an alarm if the concentration of the organic molecule exceeds a certain level. In another embodiment, the computer outputs data onto a reporting outlet such as a computer monitor. In yet another embodiment, the computer controls a feedback loop to change a process in response to variation in the concentration of the organic molecule.

In a preferred embodiment, as shown in FIG. 3, the biosensor 10 is a glucose biosensor 10 that can be implanted into the human body. In this case, the means for reporting 60 is preferably a battery powered telemeter 60 that transmits a data signal to a receiver operably connected to the computer. The computer also compares the data signal to a calibration curve and reports the concentration through a reporting means. The reporting means is preferably an audible alarm to warn diabetics if glucose levels get too high or too low. In its most preferred embodiment, the computer also controls an insulin pump to correct the blood glucose level of the diabetic. Ideally, the biosensor 10 would be used on conjunction with an implanted glucose pump and would functionally replace the pancreas in controlling blood glucose levels, allowing diabetics to lead nearly normal lives.

Figure 5:
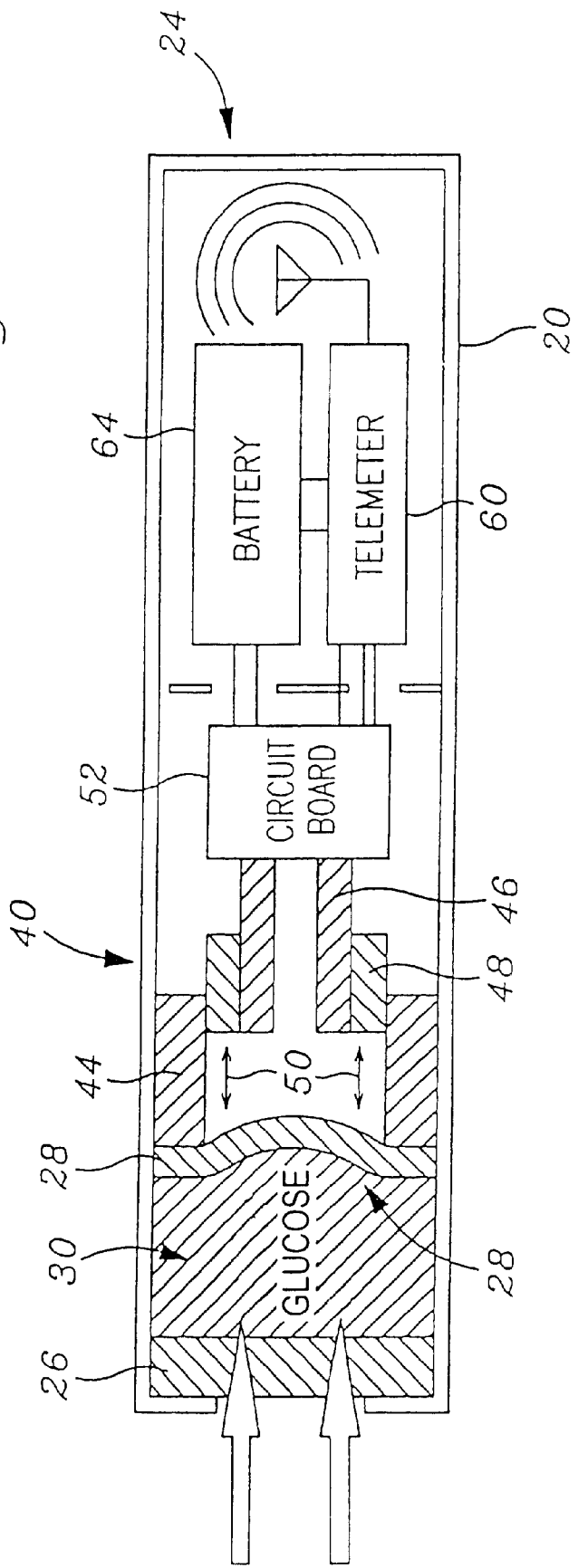
FIG. 5 is a side partial cross-sectional view of the preferred embodiment, showing glucose diffusing into the hydrogel, causing the hydrogel to swell and causing the pressure transducer to signal to a computer through a telemeter.

Method for Using a Biosensor to Measure the Concentration of Glucose in a Solution The invention further includes a method for using a biosensor 10 to measure the concentration of glucose in a solution. The method includes the following steps: First, providing a biosensor 10 as described above. Con A is chemically or physically immobilized in the hydrogel 30, preferably using chemical conjugation. The biosensor 10 is preferably first immersed in a buffer and inserted into a control solution. The data generated is then compared to a calibration curve to calibrate the biosensor 10. Once the biosensor 10 is removed and rinsed in another buffer, the biosensor 10 is inserted into the solution. The glucose molecules are allowed to diffuse into the polymeric hydrogel 30, causing competitive binding of free glucose with immobilized glucose to Con A. The competitive binding between free glucose and immobilized glucose to Con A reduces hydrogel crosslinking, which causes the hydrogel 30 to swell and exert a pressure on the diaphragm 28, as shown in FIG. 5. This swelling is measured with the means for measuring 40. The means for measuring 40 is preferably a pressure transducer 40. The pressure transducer 40 is used to measure the pressure of the hydrogel 30, which is proportional to the concentration of the free glucose level in the hydrogel 30. Data from the transducer 40 regarding this measurement is then sent to a means for reporting 60. In an implantable biosensor 10, a battery powered telemeter 60 is used to transmit the data to a computer. This can be then reported to the user through a computer monitor, an audible alarm, or a feedback system such as an automatic insulin pump (as described above) or glucagon injection pump. Throughout use, the system can be recalibrated by taking blood samples and comparing the glucose readings to those reported by the biosensor 10. The computer actuated means of calibration can then be adjusted to correct for any errors.

Operation Principle

The output of a sensor is always monitored and compared with a preset value (or threshold value). If the sensor output is out of the preset range, an alarm signal is generated. This alarm signal can be further utilized to actuate a certain alarm protocol such as automatic dialing and send a prerecorded message corresponding to the condition detected.

Figure 9:
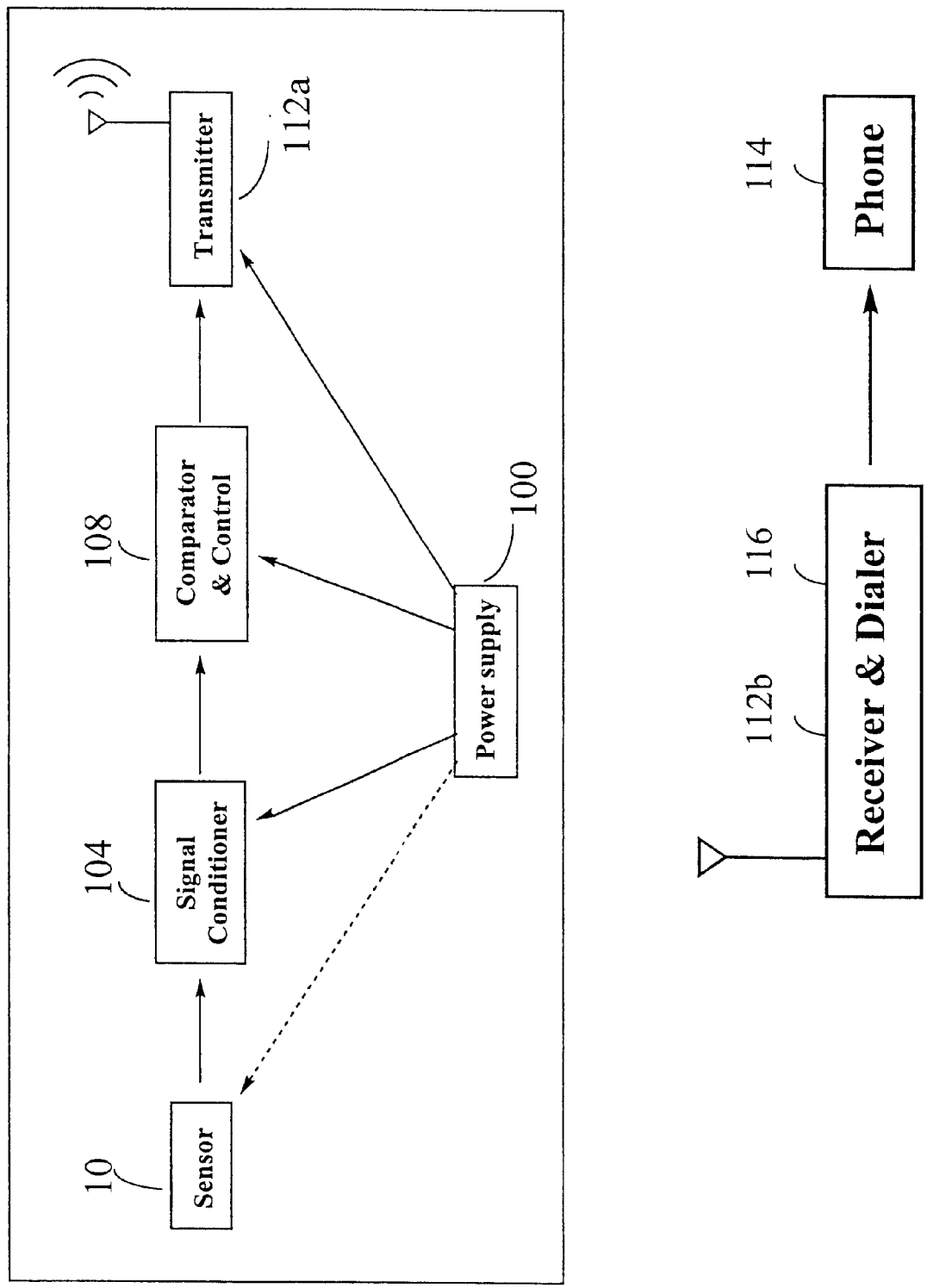
FIG. 9 is a block diagram of an automatic alarm system in conjunction with wireless actuation of dialing.
Figure 10:
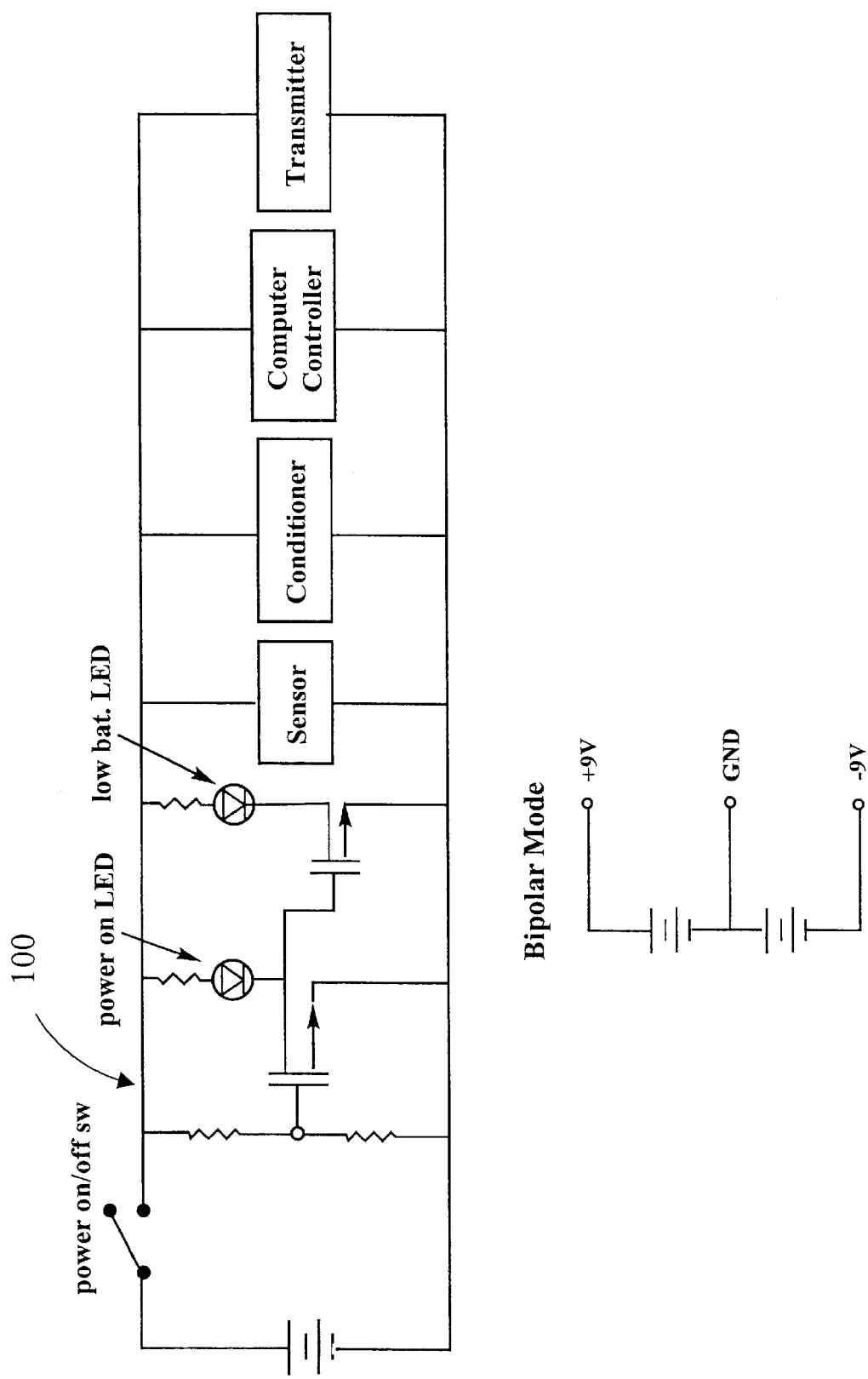
FIG. 10 is a schematic diagram of a power supply for the various portions of the automatic alarm system.

The block diagram in FIG. 9 shows a diagram of a working model for giving an alarm to diabetics and a signal to caretakers using automatic dialing and sending of a prerecorded message when blood glucose levels drop to the level of hypoglycemia.

Major Elements of the Alarm System

The major elements of an automatic alarm device are a power supply 100, a sensor (such as biosensor 10 or other sensor for monitoring a physiological condition), a signal conditioning circuit 104, a comparator circuit 108, a transmitter/receiver 112a and 112b, a dial actuator 116, and a control circuit.

Power Supply

The power supply 100 preferably provides electric energy to all the elements of the device requiring power. Considering portability of the device, a dry-cell battery is the preferred choice for supplying power. However, compatibility of the cell with power requirements of all the elements (voltage and capacity) will be somewhat determinative of the type used. As presently perceived, a large capacity 9 volt-battery is believed to be the best choice.

During the development, a bipolar power supply using 2 batteries makes the circuit design much easier. A low-battery indicator should be an essential part.

Signal Conditioning Circuit

Figure 11:
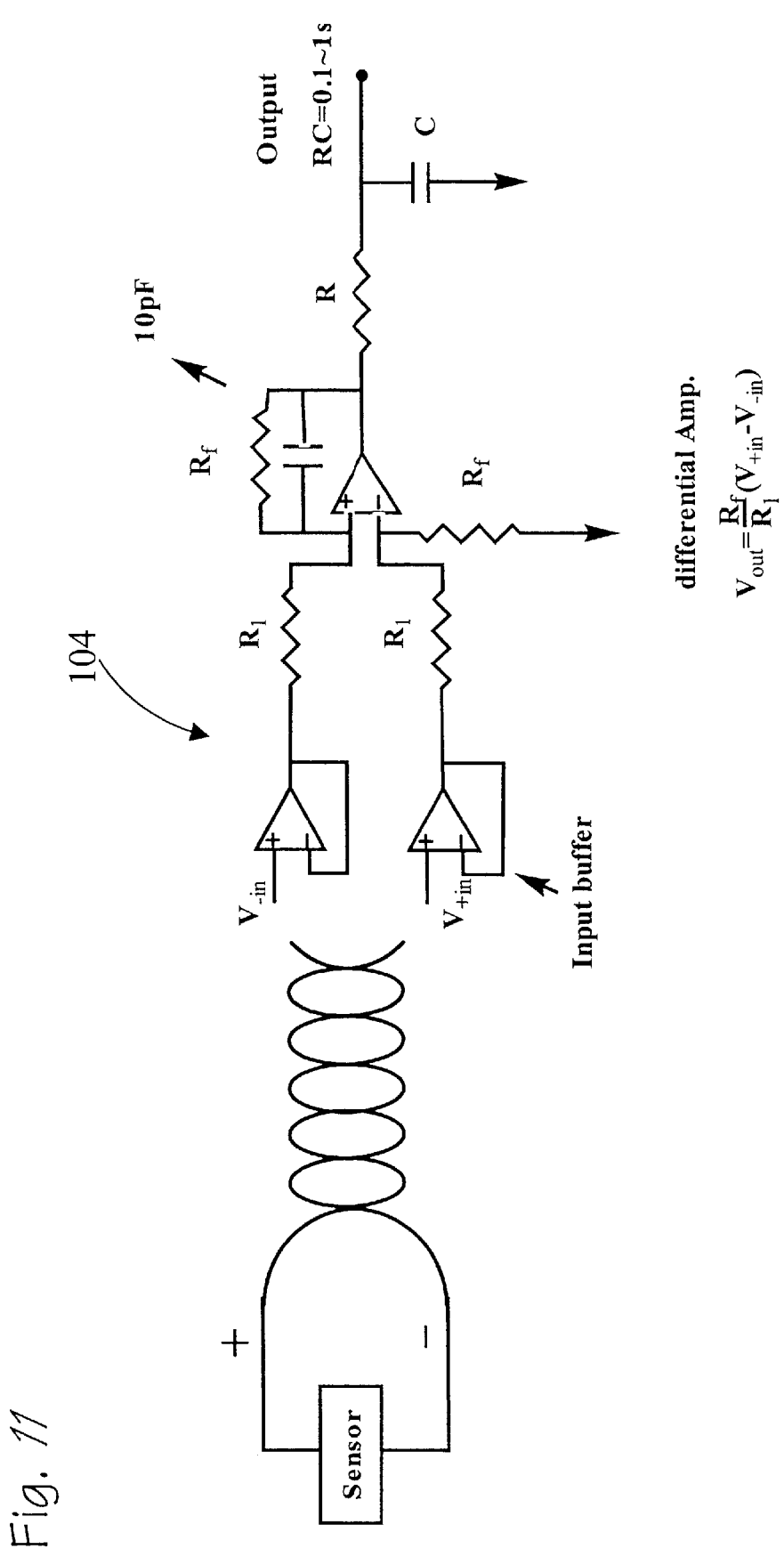
FIG. 11 is a schematic diagram of the signal conditioning circuit.

The need for the signal conditioning circuit 104 depends on the quality of the signal from the sensor. If the sensor signal comes along with a great deal of environmental noise, the signal conditioning circuit 104(FIG. 11) is necessary to operate the device in a reliable manner. Typically, a high input-impedance differential amplifier works for any kind of sensor. A prepackaged circuit, the so-called "instrumentation amplifier" is commercially available. However, for a prototype device, a quad-op amp IC (e.g., LM 384 from National Semiconductors) will serve well by providing 4 amplifiers. A differential amplifier is excellent in removing common mode noise. The gain of the differential amplifier can be adjusted to provide signals of a good linear range. A low-pass filter after differential amplification will further decrease high frequency noise. An RC time constant of 0.1 to 1 seconds is appropriate. For example, an RC time constant of 1 second can be obtained using 100 kohm and 10 F.

Comparator and Control Circuit

A comparator always compares the monitored signal (here, from the output of the signal conditioning circuit) with the preset value. The threshold value will be adjusted using a potentiometer. If the monitored signal goes over the threshold value, the output of the comparator changes its status from '0' to '1' or from 'off' to 'on'. This change of status is utilized to actuate a following digital circuit. The simplest circuit will be driving an electromechanical switch to 'on' position, by which a transmitter circuit is connected to the power supply; LM311 type comparator should best fit the purpose.

Figure 12:
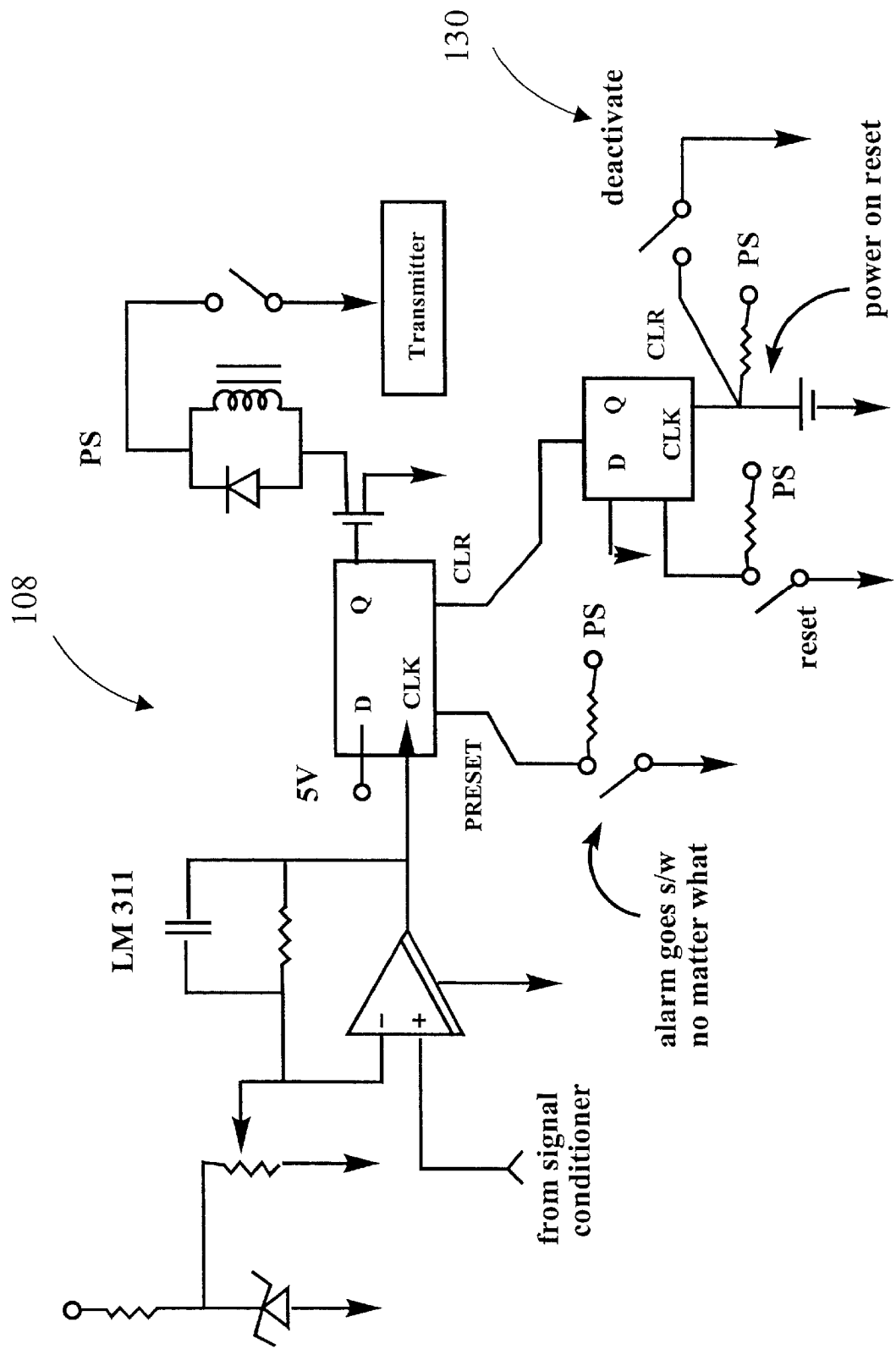
FIG. 12 is a schematic diagram of the comparator and control circuit.

The comparator circuit 108 must be with extra control circuits 130 (FIG. 12). The extra controls are for deactivating the device and resetting the device in the case when alarms are sent mistakenly or by device malfunction. Furthermore, an extra switch should be there to actuate dialing in any case at the discretion of the device user. All these factors can be achieved by using a digital D-flip-flop IC(C7474).

If necessary, the comparator circuit 108 can be used for determining if the sensor 10 operates normally as well as for alarming. If sensor output goes beyond an expected operating range including an alert level, the comparator 108 will indicate malfunction of the sensor 10.

Transmitter/Receiver

A Transmitter/receiver 112a and 112b is necessary in order to operate a phone 114 at a distance from the device-carrier (FIG. 13). Wireless activation of the phone 114 can be achieved using a typical FM method. Typically, a transmitter consists of a carrier wave generator 140, a signal generator 144, a modulator 148 to mix signal to carrier wave, a power booster 152, and a radiator 156. The carrier wave frequency may be in the range of several tens to several hundreds megahertz. The signal must be unique that the receiver picks up to avoid mistaken dialing due to environmental noises from other electronic devices. A receiver 112b operates in a reversed manner to that of a transmitter 112a. Although a transmitter/receiver, 112a/112b must be custom designed eventually, it can be adapted from a minimally modified transmitter/receiver used in kids' remote control toys. (In light of the present disclosure, those skilled in the art will appreciate that other forms of remote communication, such as electronic mail could also be used.)

Dialing

Figure 14:
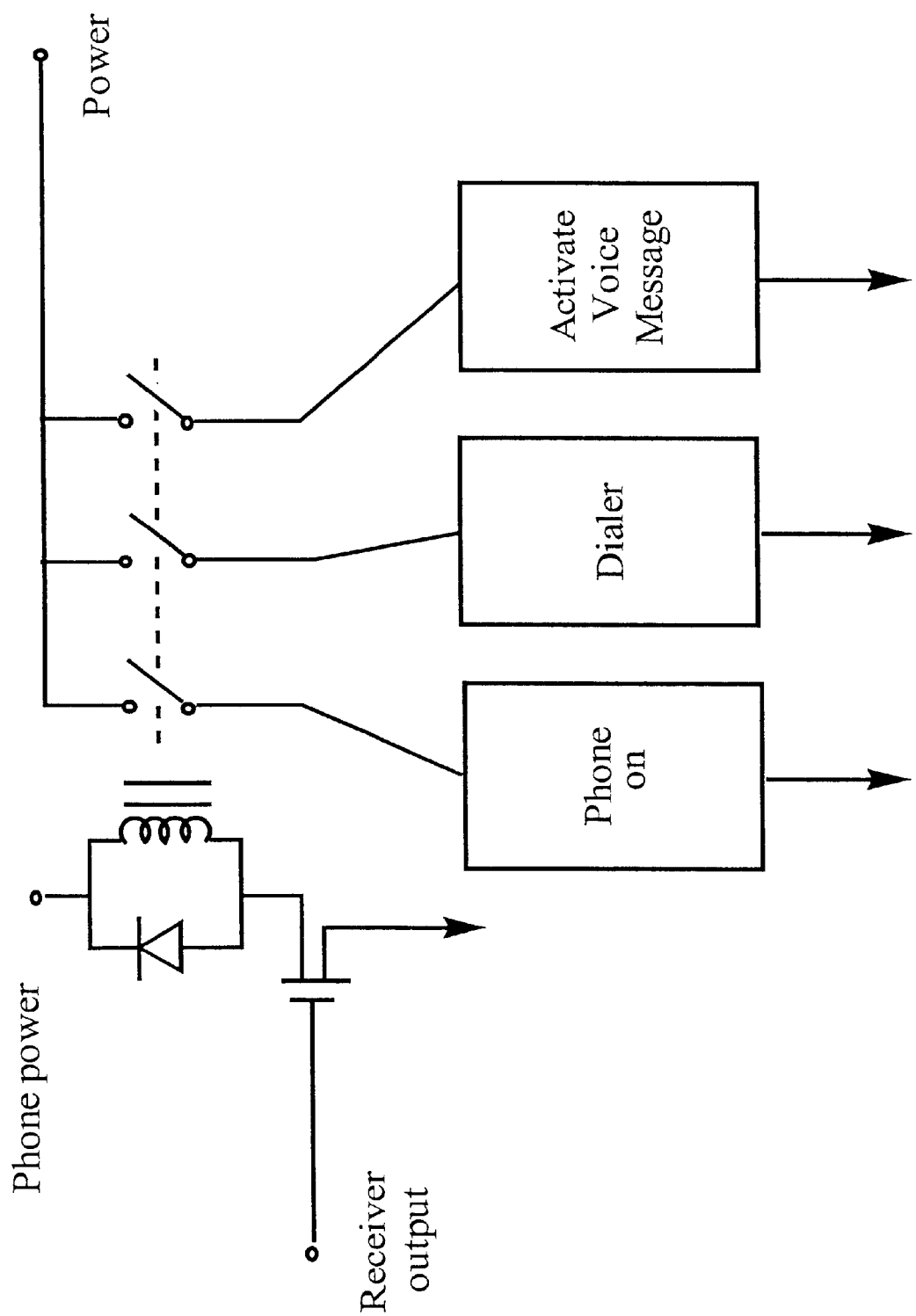
FIG. 14 is a schematic diagram of dialing mechanism.

Dialing to a remote alarm signal can be achieved in a number of ways that will be well known to those skilled in the art. A schematic of such a system is shown in FIG. 14 and those familiar with remote telephone interactions will be familiar with numerous ways of implementing this and other configurations.

Some degree of modification is necessary to allow utilization of current answering phone systems, and utilization of current answering function to dialing/messaging. Overall, everything is preferably prepared in the phone. It simply needs a sort of switching on by an alarm signal from the receiver.

Those skilled in the art will appreciate that the combination of a biosensor with an automated telephonic notification system provides significant advantages for improving health care. Not only is the patient warned of a condition which can cause physiologic damage, but also health care workers are notified if the situation surpasses a predetermined threshold. Thus, for example, if the diabetic has gone into a hypoglycemic shock, medical personnel (or relatives of the patient) can respond and provide appropriate medical care. Such a system is particularly advantageous for those who live alone and those of limited mobility.

Figure 15:
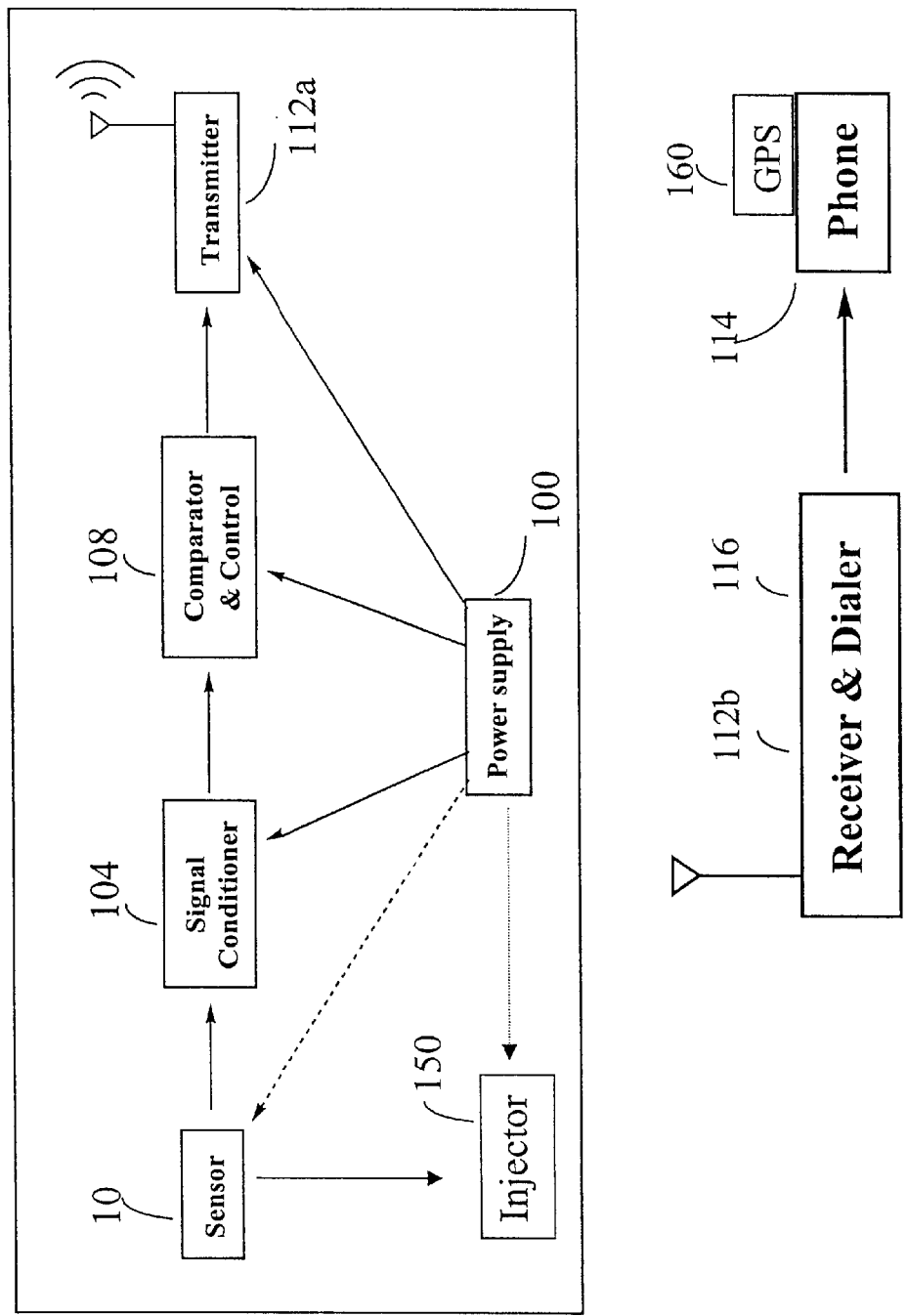
FIG. 15 is a block diagram of an automatic alarm system used in conjunction with an injection device for providing injections responsive to the alarm system.

In addition to the above, the alarm system can also function as a system for treating hypoglycemia in a diabetic. Turning to FIG. 15, there is shown a schematic of an alarm system similar to that shown in FIG. 9. The system further includes, however, an injection mechanism 150 that dispenses glucose, another sugar, or a drug into the blood stream of the patient in response to the alarm. Those skilled in the art will appreciate that the injection device 150 may provide predetermined dose, or may inject varying quantities in response to the physiological condition detected by the sensor 10. The injection device 150 may be hard wired to the system, or may be controlled by the transmitter 112a.

In addition to the injection mechanism 150, the system can also include a global positioning system 160 associated with the telephone 114 or some other position of the alarm system. The global positioning system 160 enables rapid location of the individual in the event that medical treatment is necessary. Such a system is particularly beneficial for individuals who have diabetes but still which to engage in activities such as cycling, hunting and fishing.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A biosensor for measuring the concentration of glucose, the biosensor comprising:

a polymeric hydrogel that changes its crosslinking density and swelling tendency in proportion to the concentration of free glucose;

glucose binding molecules chemically or physically immobilized in the hydrogel;

a hexose saccharide or a polysaccharide chemically or physically immobilized in the hydrogel, the free glucose competitively binds with the immobilized hexose saccharide or polysaccharide to the glucose binding molecules, which reduces the number of hydrogel crosslinks, thereby causing the hydrogel to swell and increasing the pressure exerted by the hydrogel in its enclosure;

a means for measuring the pressure or amount of swelling of the hydrogel; and a means for reporting the concentration of the glucose molecule based on the measured pressure of the hydrogel.

2. The biosensor of claim 1 further comprising a rigid enclosure containing the hydrogel, the enclosure having an open end sealed by a semipermeable membrane that allows glucose molecule to diffuse into the hydrogel.

3. The biosensor of claim 2 wherein the enclosure further includes a diaphragm, the hydrogel being enclosed between the diaphragm and the semipermeable membrane, the diaphragm working in conjunction with the means for measuring in order to monitor changes in the pressure and swelling tendency of the hydrogel.

4. The biosensor of claim 3 wherein the enclosure is conjugated with heparin and polyethylene glycol.

5. The biosensor of claim 3 wherein the enclosure is coated with a semipermeable membrane and a biodegradable polymer on the semipermeable membrane.

6. The biosensor of claim 5 wherein the biodegradable polymer is conjugated with heparin and polyethylene glycol.

7. The biosensor of claim 5 wherein the semipermeable membrane has a pore size between 0.1 to 15 $\mu$m.

8. The biosensor of claim 1 wherein the hydrogel includes crosslinking that allows small molecules such as glucose to diffuse into the hydrogel, but prevents diffusion of any macromolecules such as glycoproteins, lectins, and polysaccharides.

9. The biosensor of claim 1 wherein the biosensor includes a hexose saccharide with a vinyl group conjugated to the C1 hydroxyl group of the hexose saccharide, the vinyl group being used to chemically immobilize the hexose saccharide to the polymer backbone of the hydrogel.

10. The biosensor of claim 9, wherein the hexose saccharide is selected from the group that consists of $\alpha$-D-mannopyranoside, p-nitrophenyl-$\alpha$-D-mannopyranoside, or p-nitrophenyl-$\alpha$-D-glucopyranoside.

11. The biosensor of claim 1 wherein the hexose saccharide includes a monomer containing hexose moieties such as glycidyl acrylate, glycidyl butyl ether, glycidyl cinnamate, or glycidyl methacylate such as glycosyloxyethyl methacrylate.

12. The biosensor of claim 1 wherein the polysaccharide chemically or physically immobilized in the hydrogel is any macromolecule that contains polysaccharides, such as for example glycogen, starch, cellulose, nigeran, paramylon, luteose, mucin, and glycoproteins.

13. The biosensor of claim 1 wherein the glucose binding molecules are chosen from the group consisting of glucose oxidase, hexokinase, glucosidase, xylose. isomerase, glucose phosphorylase (glucokinase), lactate dehydrogenase, boronic acids, and lectins.

14. The biosensor of claim 13 wherein the glucose binding molecules include genetically modified proteins, which have only binding sites to glucose moieties but having no enzymatic activity.

15. The biosensor of claim 1 wherein the hydrogel is biocompatible, nontoxic, and inert in the body.

16. The biosensor of claim 1 wherein the hydrogel has porous structure to enhance diffusion of glucose into the hydrogel.

17. The biosensor of claim 1 wherein the hydrogel further includes chemically immobilized pendant groups (pKa 3–11) which are charged under physiological pH conditions, with the density of charged pendant groups chosen to optimize the amount of hydrogel swelling in response to free glucose concentration changes.

18. The biosensor of claim 1 wherein the means for measuring hydrogel pressure or swelling tendency is a pressure transducer.

19. The biosensor of claim 1 wherein the means for measuring hydrogel pressure or swelling tendency is a piezoelectric transducer or a piezoresistive pressure sensor.

20. The biosensor of claim 1 wherein the means for reporting is a battery powered telemeter that transmits a data signal to a receiver operably connected to a computer means, the computer means comparing the data signal to a calibration curve to calculate the concentration of glucose, the computer means then reporting the concentration through a reporting means.

21. The biosensor of claim 20 wherein the means for reporting is a computer electrically connected to the means for measuring, the computer comparing data from the means for measuring to a calibration curve to calculate the concentration of the glucose molecule, the computer means then reporting the concentration through a reporting means.

22. A biosensor for measuring the concentration of glucose in a person, the biosensor comprising:

a rigid, biocompatible enclosure having an open end and a closed end, the open end being covered by a semipermeable membrane;

a diaphragm being positioned between the semipermeable membrane and the closed end;

a polymeric hydrogel enclosed between the semipermeable membrane and the diaphragm, the hydrogel including moieties that cause the hydrogel to change its swelling tendency and the pressure exerted by the hydrogel on the diaphragm in proportion to the free glucose concentration of the hydrogel;

an amount of a glucose-binding molecule immobilized in the hydrogel;

an amount of a hexose saccharide immobilized in the hydrogel;

a pressure transducer operatively engaged to the diaphragm; and a battery powered telemeter operatively engaged to the transducer.

23. A biosensor for measuring the concentration of a free molecule, the biosensor comprising:

a polymeric hydrogel that changes its swelling tendency and pressure in proportion to the concentration of a free molecule; a bound molecule immobilized in the hydrogel; a high affinity and specific binding molecule chemically or physically immobilized in the hydrogel, configured such that the free molecule competitively binds with the bound molecule to the immobilized high affinity and specific binding molecule, thereby reducing the number of hydrogel crosslinks and causing the hydrogel to swell and increase the pressure of the hydrogel in the confined space;

a means for measuring the pressure or amount of swelling of the hydrogel; and a means for reporting the concentration of the free molecule based on the measured pressure of the hydrogel.

24. A system for treating hypoglycemia, the system comprising:

a sensor for disposition in a patient, the sensor being configured to monitor blood glucose levels within a patient by use of a hydrogel;

alarm circuitry disposed in communication with the sensor for warning when the blood glucose level passes outside a predetermined parameter; and an auto-injection device responsive to alarm signals for automatically injecting agents into the patient to return the blood glucose level to within the predetermined parameter.

25. A system for treating hypoglycemia, the system comprising:
   a sensor for disposition in a patient, the sensor being configured to monitor blood glucose levels within a patient;
   alarm circuitry disposed in communication with the sensor for warning when the blood glucose level passes outside a predetermined parameter;
   an auto-injection device responsive to alarm signals for automatically injecting agents into the patient to return the blood glucose level to within the predetermined parameter; and
   a global positioning system for determining the location of the patient.

26. The biosensor of claim 1, wherein the hexose saccharide is chosen from the group of hexose saccharides consisting of glucose and mannose.

27. The biosensor of claim 1, wherein the polysaccharide is chosen from the group of polysaccharides consisting of mucin, glycogen, and glycoproteins.

28. The biosensor of claim 13, wherein the lectins are chosen from the group of Con A and isolectin I.

29. The biosensor of claim 1, additionally including means for generating an alarm signal responsive to the reported concentration of the glucose if outside a predetermined range, and a transmitter for transmitting the alarm signal to a remote location.

30. The biosensor of claim 29, additionally including a receiver for receiving alarm signals from the transmitter, and a dialer for dialing a telephone in response to an alarm signal received from the transmitter.

31. The biosensor of claim 29, additionally including an injection device for injecting agents into a person in response to alarm signals from the means for generating an alarm signal.

32. The biosensor of claim 1, additionally including an injection device for injecting agents into a person in response to reported concentration of the glucose.

* * * * *